United States Patent
Ford et al.

(10) Patent No.: US 11,717,371 B2
(45) Date of Patent: Aug. 8, 2023

(54) INSTRUMENT PROTECTOR BACKER CARD

(71) Applicant: SterileBits, Inc., Marina Del Rey, CA (US)

(72) Inventors: Craig Ford, Marina del Rey, CA (US); Guy Brent Phipps, Long Beach, CA (US); Robert James Jones, Cedar Park, TX (US); William Lawrence Patton, III, Rancho Mirage, CA (US)

(73) Assignee: SterileBits, Inc., Kemah, TX (US)

( * ) Notice: Subject to any disclaimer, the term of this patent is extended or adjusted under 35 U.S.C. 154(b) by 0 days.

(21) Appl. No.: 17/160,816

(22) Filed: Jan. 28, 2021

(65) Prior Publication Data

US 2021/0236225 A1 Aug. 5, 2021

Related U.S. Application Data

(60) Provisional application No. 62/969,267, filed on Feb. 3, 2020.

(51) Int. Cl.
| | | |
|---|---|---|
| A61B 50/30 | (2016.01) | |
| B65D 75/52 | (2006.01) | |
| A61B 17/28 | (2006.01) | |
| A61B 90/90 | (2016.01) | |

(52) U.S. Cl.
CPC ............ *A61B 50/30* (2016.02); *B65D 75/525* (2013.01); *A61B 17/28* (2013.01); *A61B 90/90* (2016.02)

(58) Field of Classification Search
CPC ... A61B 50/30; A61B 50/20; A61B 2050/314; A61B 2050/0056; A61B 2050/0065; A61B 2050/318; B65D 73/0021; B65D 73/0035; B65D 73/0042; B65D 73/0064; B65D 73/0014; B65D 73/0078; B65D 73/0085
USPC ................ 206/495, 806, 477–479, 482, 363
See application file for complete search history.

(56) References Cited

U.S. PATENT DOCUMENTS

| | | | |
|---|---|---|---|
| 2,118,144 A | | 8/1932 | Berman et al. |
| 3,098,751 A | | 7/1963 | Huyck et al. |
| 3,487,922 A | | 1/1970 | Peck |
| 3,604,616 A | | 9/1971 | Greif |
| 3,925,014 A | | 12/1975 | Langdon |
| 3,991,881 A | * | 11/1976 | Augurt .................. B65D 75/52 206/439 |
| 4,023,678 A | * | 5/1977 | Fiedler ...................... A61F 6/14 206/476 |
| 4,043,754 A | | 8/1977 | Sklar |
| 4,142,632 A | * | 3/1979 | Sandel .................. A61B 50/20 206/478 |
| 4,229,420 A | | 10/1980 | Smith et al. |
| 4,247,003 A | * | 1/1981 | Jones ........................ G09F 1/02 206/486 |
| 4,385,692 A | * | 5/1983 | Eldridge, Jr. .......... A61B 50/30 206/363 |
| 4,506,787 A | * | 3/1985 | Bruso .................... A61B 50/20 206/363 |

(Continued)

*Primary Examiner* — Robert Poon
(74) *Attorney, Agent, or Firm* — Kelly and Kelley, LLP

(57) ABSTRACT

An instrument protector backer card provides enhanced structural integrity of a sterile package solution for medical instruments. A mounting surface has a strap for holding a removable medical instrument. A shield member is movable from a non-deployed position into a deployed position to define an open-ended pocket to receive an end of the medical instrument therein. A flap may be used to hold jointed medical instrument in an open position.

26 Claims, 10 Drawing Sheets

(56) References Cited

U.S. PATENT DOCUMENTS

| | | | | |
|---|---|---|---|---|
| 4,597,493 | A | * | 7/1986 | Bruso ................. B65D 73/0021 206/478 |
| 5,351,822 | A | * | 10/1994 | Sinn ................... B65D 73/0021 206/478 |
| 5,375,717 | A | * | 12/1994 | Roshdy ................ B65D 81/056 206/464 |
| 5,477,964 | A | * | 12/1995 | Hart ................... B65D 73/0021 206/483 |
| 5,601,189 | A | * | 2/1997 | Roshdy ............. B65D 73/0021 206/363 |
| 5,655,657 | A | * | 8/1997 | Roshdy ................. A61B 50/30 206/363 |
| 5,791,470 | A | * | 8/1998 | Usui ................. B65D 73/0014 206/362.4 |
| 9,439,658 | B2 | | 9/2016 | Ford et al. |
| 2006/0016707 | A1 | * | 1/2006 | Chow .................... B65D 85/04 206/395 |
| 2009/0065386 | A1 | * | 3/2009 | Hasegawa ............. A47F 5/0006 206/349 |
| 2013/0043155 | A1 | * | 2/2013 | Hartley ................. A61B 50/39 206/363 |
| 2014/0103100 | A1 | * | 4/2014 | Falcon ............... B65D 73/0085 229/122 |
| 2014/0343553 | A1 | * | 11/2014 | Ford ................. A61B 17/1628 606/80 |
| 2015/0223537 | A1 | * | 8/2015 | Kim ....................... A41G 5/004 206/581 |
| 2018/0296297 | A1 | * | 10/2018 | Moloney ............. B65D 75/366 |

\* cited by examiner

INSTRUMENT PROTECTOR BACKER CARD

RELATED APPLICATIONS

This application claims the benefit of U.S. Provisional Application No. 62/969,267, filed on Feb. 3, 2020.

FIELD OF THE INVENTION

This invention relates generally to packaging techniques and retaining devices for medical instruments. More particularly, this invention relates to a retaining device usable for protecting medical instruments during and after sterilization while providing for visual identification of the instrument.

BACKGROUND OF THE INVENTION

As is well known in the medical profession, the sterilization of precision medical instruments must be accomplished with certain purposes in mind. Basically, for both economic and efficiency reasons, such sterilization needs to be done in a manner which will ensure the most effective exposure of the instrument to the sterilizing medium while minimizing the possibility of contaminating the instrument prior to its use. Obviously, a major concern in this process is the actual handling of the instrument. In order to meet the need for effective handling of a medical instrument during sterilization, various packaging techniques have been proposed. The prior art devices, however, do not incorporate into one package all of the features which are deemed desirable for the most effective handling of a medical instrument between the time it is sterilized and its subsequent use.

One desirable feature of an instrument protector is that it immobilize the instrument. Such immobilization, particularly for medical instruments which are pointed or which have cutting edges, reduces the possibility of dulling or blunting their surfaces by contact with or rubbing against other surfaces. Sometimes, tip protectors are placed over the cutting ends or edges of the medical instrument. However, the tip protector's tight fit onto the instrument creates doubt as to whether the instrument gets sterilized completely. It is recommended not to use clear or colorless tip protectors in order to protect against the chance of retained surgical items in the wound by inadvertently leaving the tip protector on the medical instrument. The tip protectors are typically comprised of a plastic material, and the tip protectors and the labor required to attach and detach them may make them less convenient and more expensive than sterilization cards.

Another desirable feature is that the instrument protector present the instrument for sterilization in a configuration which will allow the greatest exposure of the instrument to the sterilizing medium. For jointed instruments this means supporting them with the blades or extension members in a separated condition. The joint Commission on Accreditation of Healthcare Organizations (JCAHO) is a non-profit organization based in the United States that accredits over twenty thousand healthcare organizations and programs in the country. JCAHO mandates that any "hinged" instrument, such as forceps, hemostats, etc., must be sterilized in the open position so that all areas of the instrument are exposed to the sterilant (steam/pressure/etc.).

Additionally, it is desirable if some provision is made for easy identification of the instrument. Preferably, such identification can be done visually and thus obviate the use of external labels which may cause confusion if the protector is used with a different instrument. This last consideration is particularly important when it is envisioned that any particular embodiment of a sterilizable instrument protector can be used with a plurality of different instruments.

Use of the instrument protector must be effective regardless of the particular sterilization process utilized. Yet another desirable feature for an instrument protector is the added protection it can give against an inadvertent puncturing of the outer sterilizable envelope by the instrument's sharp or pointed surfaces.

Several containers and devices for holding medical instruments during sterilization processes are well known in the art. For example, U.S. Pat. No. 4,229,420 issued to Smith et al., U.S. Pat. No. 4,043,754 issued to Sklar and U.S. Pat. No. 3,925,014 issued to Langdon are directed to surgical instrument racks for holding medical instruments during sterilization. These inventions are, however, designed for the collective sterilization of complete sets of instruments and do not provide the versatility and flexibility achieved by sterilizing instruments in separate packages. Furthermore, when a plurality of instruments ae simultaneously sterilized on the racks of these inventions, the retrieval of one instrument requires the exposure and possible contamination of all the others.

U.S. Pat. No. 4,385,692 issued to Eldridge entitled "Surgical Instrument Tip Protector and Method of Manufacture" discloses a protector for individual surgical instruments made of a sterilizable fine pore foam having a transparent window portion to permit identification of the instrument. This patent does not, however, teach or suggest the provision of means for retaining jaw-type jointed instruments, such as a scissors, in a blade separated position during the sterilization process. Further, the protector disclosed in this patent is made of a fine pore foam which, if snagged by the instrument, could cause particulate contamination. Also, it does not provide for a protector having a rigid support that facilitates its insertion into and immobilization within a sterilizable envelope of the type disclosed in U.S. Pat. No. 3,604,616 issued to Greif. Additionally, the instrument protector disclosed in this patent does not provide a suitable substratum on which chemical indicator inks can be imprinted.

U.S. Pat. No. 4,142,632 to Sandel entitled "Surgical Instrument Holder and Instrument Tip Protector Device" discloses a device made of a reticulated material which employs straps to hold an instrument thereon. Further, this patent suggests doubling back part of its base member and pushing it between the open handles of a surgical scissors to maintain the scissors tip portions in an open position. However, unlike the present invention, this patent does not employ a flap, integral with the base of the device, which can be folded and wedged between the open handles of the instrument and then inserted under the strap to secure the jointed instrument to the base of the device.

For non-jointed instruments, such as scalpels and probes, the concerns are essentially the same as those discussed previously. With these instruments, however, the primary concern is to provide a stable support for the instrument which immobilizes the instrument on the support while permitting visual identification of the instrument. Whereas U.S. Pat. No. 3,487,922 issued to Peck is directed to a cutlery display package having a transparent sheath, this patent does not suggest that its invention be used for sterilization of medical instruments. Moreover, it has certain distinguishable structural differences from the present invention. Specifically, the patent to Peck does not teach or suggest the use of die cut slits in the support to form a retaining strap for the instrument being protected.

Insofar as containers are concerned, U.S. Pat. No. 3,604,616 issued to Greif discloses a peel-open sterilizable envelope for retaining articles before, during and after sterilization. The patent also provides for an envelope which maintains sterility of the envelope's contents for extended periods of time. Although the invention of U.S. Pat. No. 3,604,616 allows for individual treatment of medical instruments, it does not teach or suggest means which would ease insertion of the instrument into the sterilizable envelope. Also, the patent does not teach a rigid support for immobilizing the medical instrument during the sterilization process.

U.S. Pat. Nos. 4,506,787 and 4,597,493 to Bruso disclose an instrument protector for protecting medical instruments during sterilization and subsequent handling. These protector cards have several drawbacks, however. A clear plastic sheet is attached to the protector card which forms a pocket into which a sharp end or working end of the medical instrument is inserted. While the sheet is typically transparent so as to enable identification of the medical instrument, the end of the medical instrument will at times puncture through the clear plastic sheet. There are also concerns of whether the sterilant will adequately enter into the pocket created by the clear plastic sheet. Another disadvantage of the instrument protector disclosed by these patents is that the jointed instrument is not always held open during or after sterilization, which can adversely impact sterilization and result in violations.

Accordingly, there is a continuing need for an instrument protector which immobilizes the instrument and retains a jointed instrument in the open position both during and after sterilization. There is also a continuing need for an instrument protector which allows the greatest exposure of the instrument to the sterilizing medium without inadvertent puncturing. Such an instrument protector should be usable with a plurality of different instruments and allow for easy identification of the instrument. What is also needed is an instrument protector which is convenient and easy to use and relatively inexpensive. The present invention fulfills these needs and provides other related advantages.

SUMMARY OF THE INVENTION

The present invention is related to an instrument protector backer card. More particularly, the present invention is directed to a sterilizable backer card for protecting medical instruments and the like.

The backer card of the present invention generally comprises a support member. The support member has a strap formed integrally therewith for holding the removable medical instrument to the support member. A first medical instrument receiving slot and a spaced apart second medical instrument receiving slot may be formed in the support member intermediate first and second ends of the support member and which cooperatively define the strap.

A flap may be formed by partial severance of the support member. The flap may be defined by a die cut formed in the support member. The flap is insertable within the first medical instrument receiving slot to hold a jointed medical instrument in an open position on the support member. One or more score lines may be formed on the flap to facilitate bending of the flap and insertion of the flap into the first medical instrument receiving slot. A central portion of the first and second medical instrument receiving slots may be larger than side portions of the slot to accommodate receipt of the medical instrument through the medical instrument receiving slot.

A shield member is connected to an end of the support member and movable between a non-deployed position and a deployed position. The shield member may be connected to the support member along a fold at the second end thereof. The shield member may be foldable with respect to the support member between the non-deployed position extending away from the support member and a deployed position adjacent to the support member. The support member and the shield member may cooperate to define an open-ended pocket that receives an end of the medical instrument when the shield member is in the deployed position. The shield member may include tabs insertable into shield tab slots formed in the support member for holding the shield member adjacent to the support member in the deployed position.

The pocket may include a sterilant window. The sterilant window may comprise a cutout formed in the shield member. The sterilant window enables unobstructed contact of sterilant to the end of the medical instrument within the pocket during sterilization of the medical instrument.

A fingerhold aperture may be formed in the support member. Typically, the fingerhold aperture is formed in the support member in spaced relation to the flap, such as adjacent to the first end of the support member.

The backer card, including the support member, may be comprised of a 14-pt. paper material. The paper material may be a bleached sulfate paper material. A paper material of this thickness and characteristics enables articulation in accordance with the present invention while retaining a jointed medical instrument in an open position during sterilization and after sterilization.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings, for purposes of illustration, the instrument protector backer card of the present invention, generally referred to by the reference number 100, is a backer board component that provides enhanced structural integrity of a sterile package solution for instruments, such as surgical instruments and/or implants. The instrument protector backer card 100 provides a mounting surface intended to hold and maintain an instrument intended for packaging and sterilization. The instrument backer card 100 of the present invention has many benefits and advantages, including securely holding the instrument to the backer card and for jointed instruments holding such instrument in an open position both during sterilization and afterwards so as to meet the JCAHO guidelines and requirements.

Figure 1:
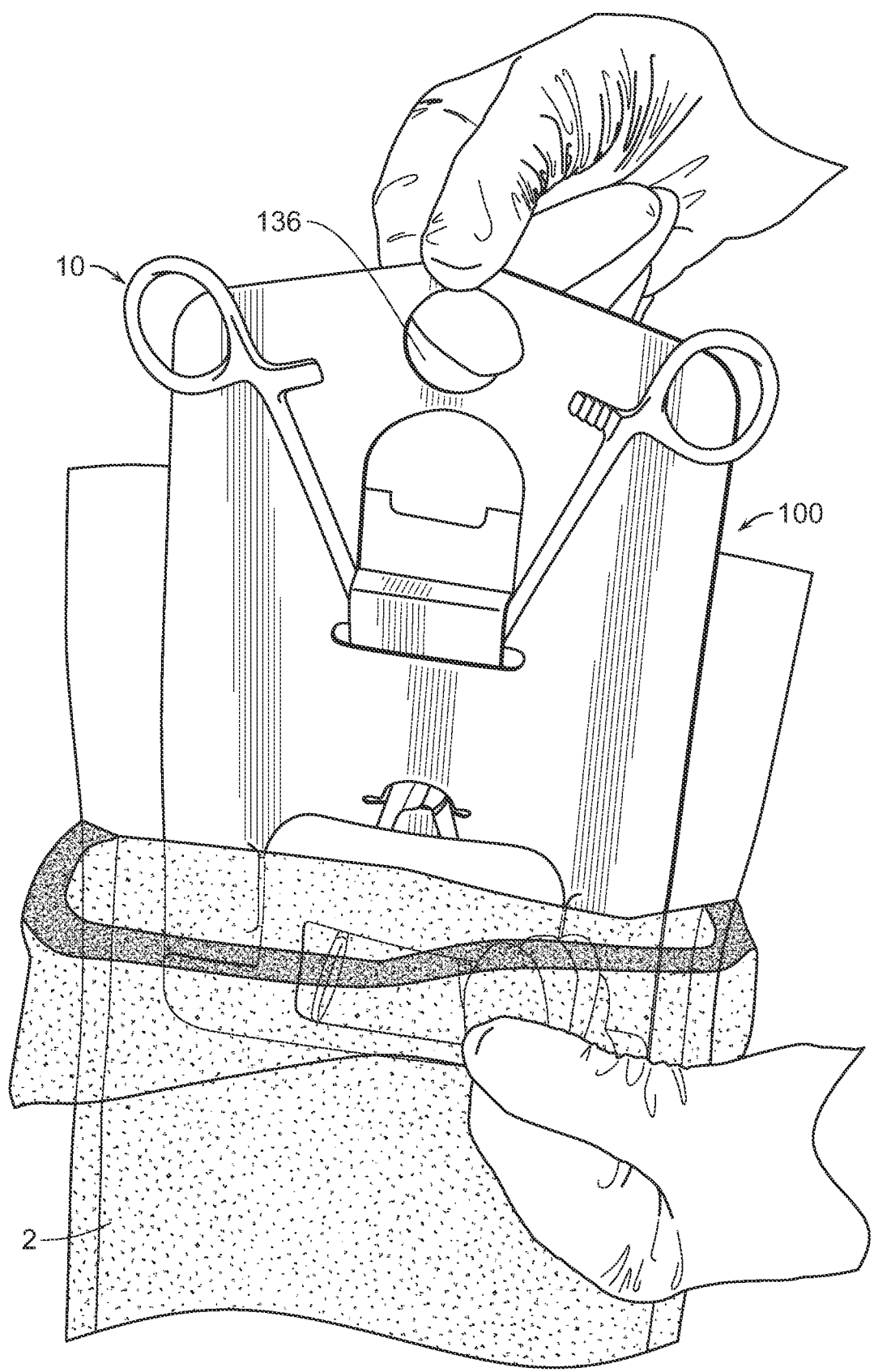
FIG. 1 is a perspective environmental view illustrating a backer card embodying the present invention supporting an instrument and being removed from a peel pouch, in accordance with the present invention.

With reference now to FIG. 1, an instrument backer card 100 embodying the present invention is illustrated holding an instrument 10 thereon and in an open position and being inserted or removed from a sterile barrier, such as a peel pouch or blister 2. The backer card 100 of the present invention enhances the sterile barrier integrity by limiting product movement within the pouch 2 or other sterile barrier package. Limiting movement within the sterile barrier package minimizes the possibility for the instrument to break and/or violate a sterile barrier (i.e., pouch) material, seals and/or borders. As will be more fully explained herein, the backer card 100 of the present invention also includes a feature which facilitates the removal of the backer card 100 and attached instrument 10 from the peel pouch 2 or other sterile barrier package.

Figure 2:
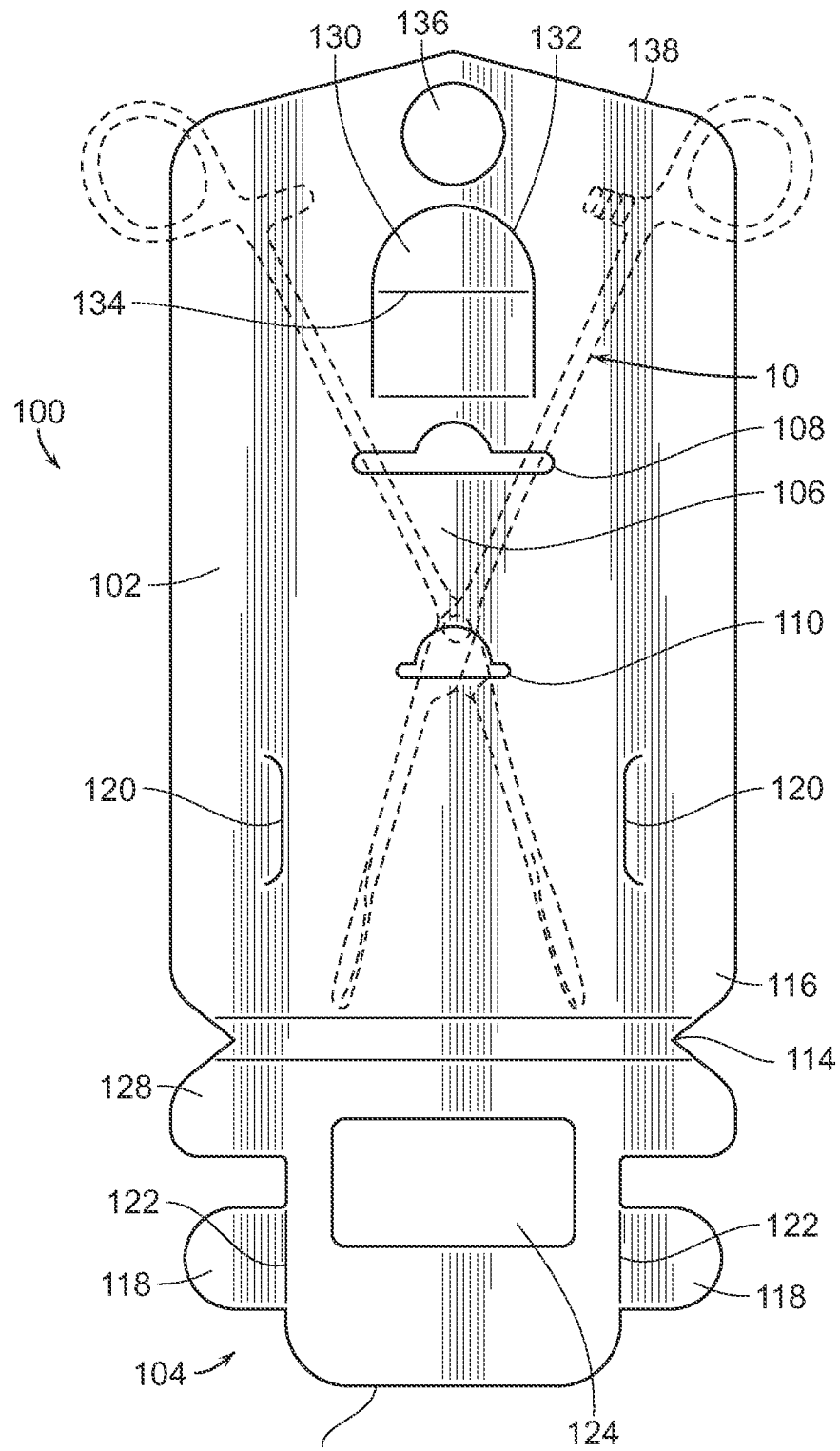
FIG. 2 is a top view of a backer card in an unfolded state and an instrument in phantom.
Figure 3:
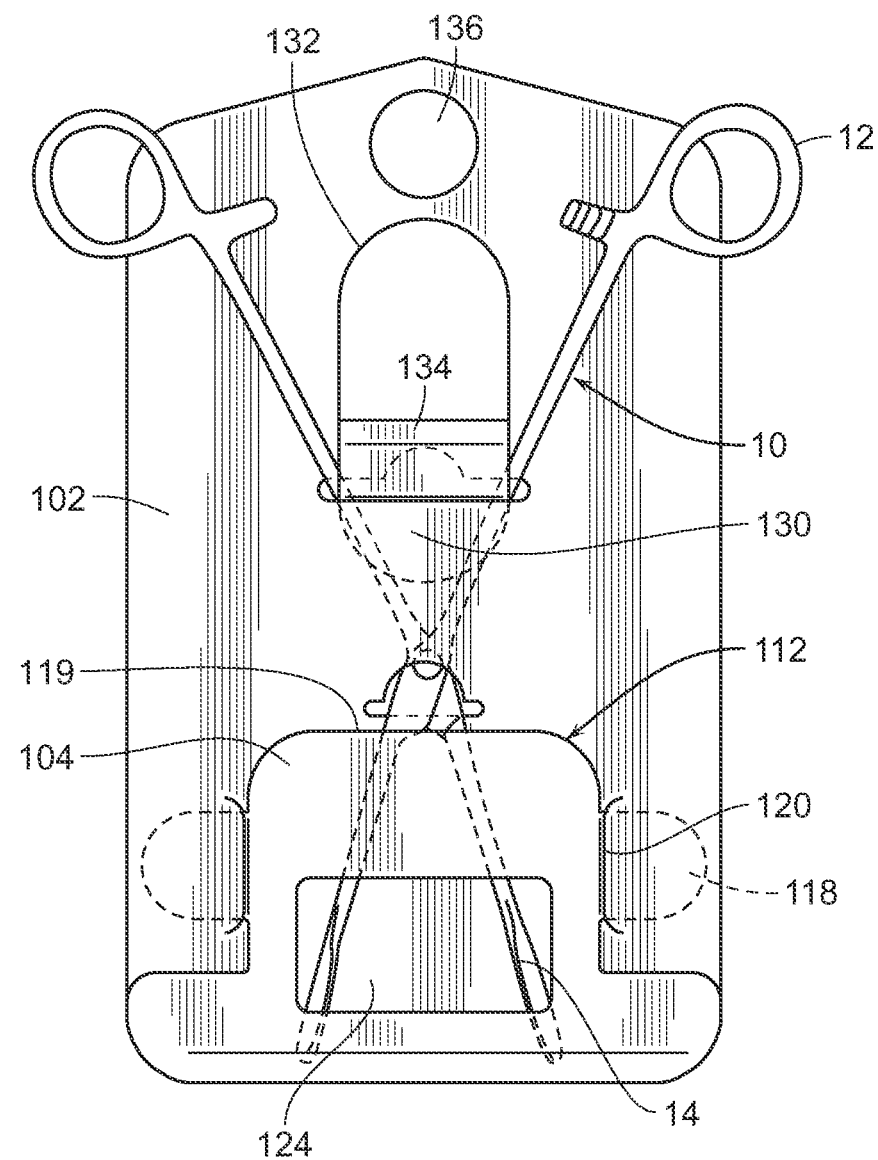
FIG. 3 is a top view similar to FIG. 2, illustrating an instrument secured to the backer card, in accordance with the present invention.

With reference now to FIGS. 2 and 3, a sterilizable backer card 100 for holding and protecting a medical instrument 10 is shown. The backer card 100 is comprised of a material which can be printed and/or die cut, subjected to sterilizing steam and/or chemicals, and which can securely and protectively hold an instrument 10, typically a medical or surgical instrument or the like, thereon during the sterilization process and thereafter before use. The backer card 100 of the present invention is comprised of a paper material of a sufficient thickness so as to securely hold the instrument 10 thereon and in an open position while sufficiently thin so as to enable certain aspects of the backer card 100 to be bent, folded, and the like manually by the user when attaching the instrument 10 thereto. In a particularly preferred embodiment, the instrument protector backer cards 100 are comprised of solid bleached sulfate (SBS), which is a bleached virgin fiber grade of paperboard of high quality. It has been found that using a 14-pt. paperboard material enables the user to manually manipulate and articulate portions of the backer card 100 while retaining the medical instrument 10 securely on the backer card 100, and retaining jointed medical instruments, such as illustrated in FIGS. 2 and 3, in an open position both during sterilization and after sterilization so as to meet the guidelines and requirements set forth by JCAHO. The SBS paperboard material is steam sterilization and ethylene oxide (EO) friendly.

With continuing reference to FIGS. 2 and 3, a sterilizable instrument protecting backer card 100 is shown. In FIG. 2, the backer card 100 is in an unfolded state. The backer card 100 generally comprises a support member 102 having a shield member 104 connected to an end of the support member. The support member has a strap 106 formed integrally therewith for holding the removable medical instrument 10 to the support member 102.

Typically, as illustrated, a first medical instrument receiving slot 108 is formed through the paperboard of the support member 102 and a second medical instrument receiving slot 110, also formed through the paperboard of the support member 102 are spaced apart from one another and cooperatively define the strap 106. As can be seen in the various figures, including FIGS. 2 and 3, the medical instrument 10 is inserted through the first medical instrument receiving slot 108 and then through the second medical instrument receiving slot 110, such that a portion of the medical instrument 10 is disposed on one surface of the support member 102, while the remainder of the medical instrument 10 is disposed on the opposite surface of the support member 102 as defined by the strap 106 between the first and second instrument receiving slots 108 and 110.

With continuing reference to FIGS. 2 and 3, the shield member 104 is movable between a non-deployed position, extending away from the support member 102, as illustrated in FIG. 2, to a deployed position adjacent to the support member 102, as illustrated in FIG. 3. When in the deployed position, as illustrated in FIG. 3, a second end of the support member 102 and the shield 104 cooperatively define an open-ended pocket 112 that receives an end of the medical instrument 10. More particularly, the shield member 104 is connected to the support member 102 along a fold 114 at a second end 116 of the support member 102. Spaced apart folds 114, as illustrated, create a wider pocket or a pocket of varying width. The shield member 104 is foldable with respect to the support member 102 between the non-deployed position and deployed position, as mentioned above to create the open-ended pocket 112. When in the deployed position, as illustrated in FIG. 3, a free end 117 of the shield member 104 and the support member 102 cooperate to define an opening 119 to the pocket 112 that receives an end of the medical instrument. The opening 119 extends substantially a length of the free end 117 of the shield member 104. The opening 119 to the pocket 112 is sized and configured to receive ends of a medical instrument of varying sizes or extended or open ends of hinged medical instruments, as illustrated herein.

The shield 104 is attachable to the support member 102 in order to retain it in the deployed position forming the pocket 112. This may be done, for example, by inserting tabs 118 of the shield 104 into shield tab slots 120 formed through the support member 102. Score lines 122 may be formed as part of the tabs 118 to facilitate bending the tabs 118 for insertion into the shield tab slots 120.

The medical instrument 10 has a first end 12, which may be comprised of handles or the like, and a second end 14 which may comprise a blade portion or sharp end or working end or the like of the instrument 10. The second end 14 of the instrument 10 is disposed within the pocket 112. Thus, the sharp or pointed edges of the second end 14 of the instrument 10 are covered so as to prevent them from puncturing or damaging the peel pouch or other sterile package 2 into which they will be placed. This arrangement also protects users handling the backer card 100 and attached instrument 10 or any other surfaces and objects which the instrument 10 attached to the backer card 100 may come into contact with.

Preferably, the pocket 112 includes a sterilant window 124 that enables unobstructed contact of sterilant to the end 14 of the medical instrument 10 within the pocket 112 during sterilization of the medical instrument. The sterile window 124 may be comprised of a cutout in the shield member. The window 124 also serves to assist users, such as medical personnel, in identifying the type of instrument 10 being held by the backer card as at least a portion of the second end 14 of the instrument 10 is visible through the window 124. Prior art instrument protectors utilize a transparent plastic sheet to create a pocket into which the second end of the instrument is inserted. However, while the second end of the instrument is viewable through the transparent plastic sheet, it is not uncommon for the second end of the instrument to puncture or tear the plastic sheet. Moreover, sterilant is only passable through an open end of the pocket in such prior art devices, potentially limiting the exposure of the sterilant to the second end 14 of the instrument 10.

With continuing reference to FIGS. 2 and 3, the shield member 104 has a first end portion 126 which my be narrower in width than a second end or portion 128 adjacent to the second end 116 of the support member 102. Preferably, the second end portion 128 is approximately the width of the support member 102. In this manner, the pocket 112 can accommodate the second end 14 of various instruments 10 as the space defined by the pocket 112 at the second end 116 of the support member 102 and second end 128 of the shield 104 provides a compartment which can accommodate the second ends 114 of instruments 10 in varying states of extension, size, etc. Thus, while the backer card 100 of the present invention may be offered in differing sizes to accommodate various sized instruments 10, each backer card 100 may be designed and configured so as to hold a variety of instruments, each having different configurations and sizes.

When the instrument 10 is hinged or includes a joint, such as hemostats, forceps, and the like, the instrument 10 must be opened and held in the open position during and after sterilization to ensure that all surface areas of the instrument are exposed to the sterilant during sterilization. A flap 130, formed by partial severance of the support member, such as at a die cut 132 formed in the support member 102. The flap 130 is insertable into the first medical instrument receiving slot 108 to hold the jointed medical instrument 10 in an open position on the support member, as illustrated in FIG. 3. One or more score lines 134 may be formed on the flap to facilitate bending of the flap 130 and insertion of the flap 130 into the first medical instrument receiving slot 108. The flap 130 prevents the arms of the instrument 110 from pivoting closed, and thus keeps the instrument 10 in an open position during sterilization, and thereafter.

A fingerhold aperture 136 is formed in the support member 102 in spaced relation to the flap 130. Typically, the fingerhold aperture 136 is formed adjacent to a first end 138 of the support member 102. The fingerhold aperture 136 is of a diameter sufficient so that a user may insert at least one finger therethrough so as to hold and lift the instrument backer card 100. This is particularly useful, as illustrated in FIG. 1, when either inserting, and more particularly removing, the instrument backer card 100 and attached instrument 10 into or out of a peel pouch or other sterilization package 2. In the past, sterilized instruments have been dumped onto a sterile field when being removed from the pouch 2, risking contamination of the field. Incorporation of the fingerhold aperture 136, however, enables the user a place to grab the backer card 100 and safely pull it from the peel pouch 2.

Figure 4:
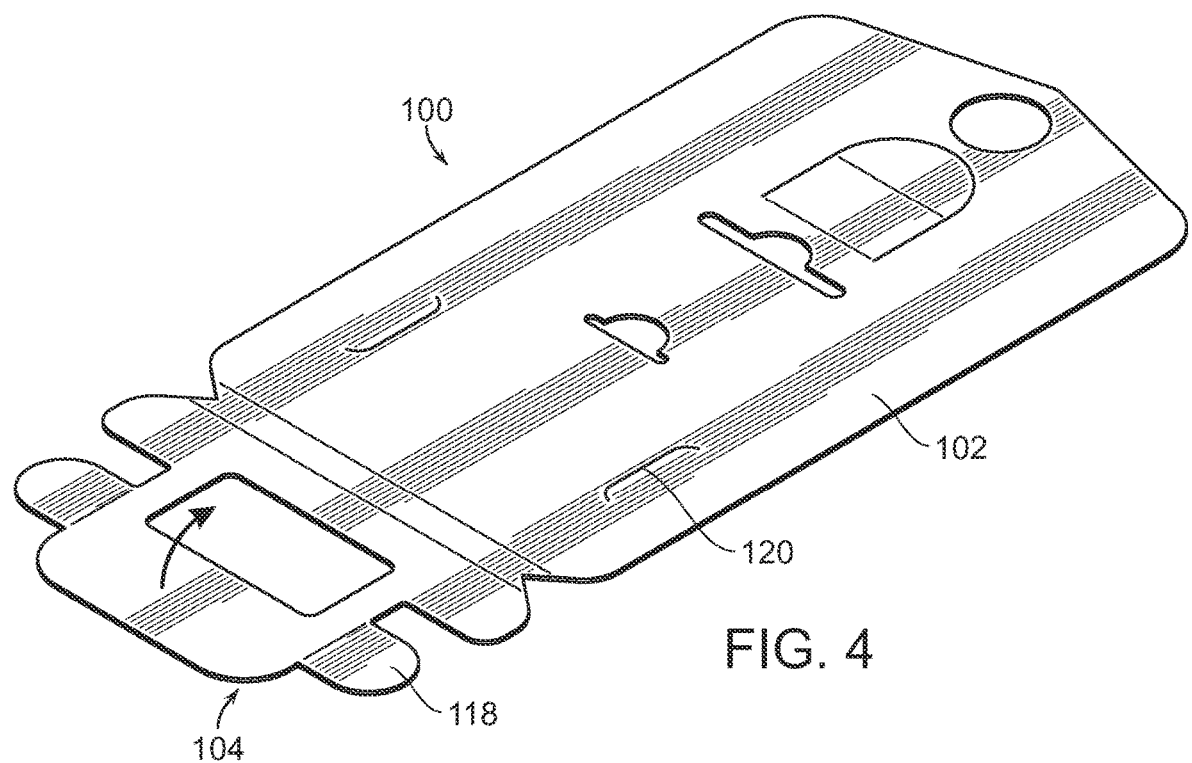
FIGS. 4 and 5 are top perspective views illustrating the deployment of a shield to create a pocket in accordance with the present invention.
Figure 5:
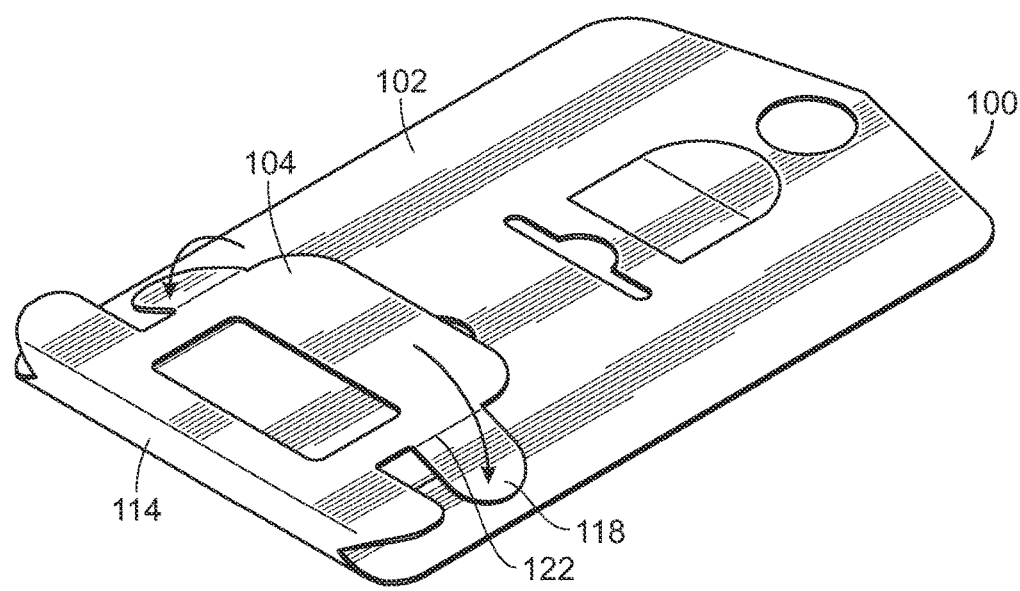

With reference now to FIGS. 4-8, the assembly and attachment of an instrument to the backer card 100 is shown. FIG. 4 illustrates the backer card 100 in a generally planar state, with the shield 104 in the non-deployed position and extending away from the support member 102. The shield member is moved, as shown by the arrow in FIG. 4, and pivoted towards and adjacent to the support member 102, as illustrated in FIG. 5. Tabs 118 are folded along score line 122 and inserted into the shield tab slots 120 of the support member 102, as illustrated by the arrows in FIG. 5. Insertion of the tabs 118 into the shield tab slots 120 hold the shield member 104 adjacent to the support member 102 in the deployed position so as to cooperatively form a pocket, as mentioned above.

Figure 6:
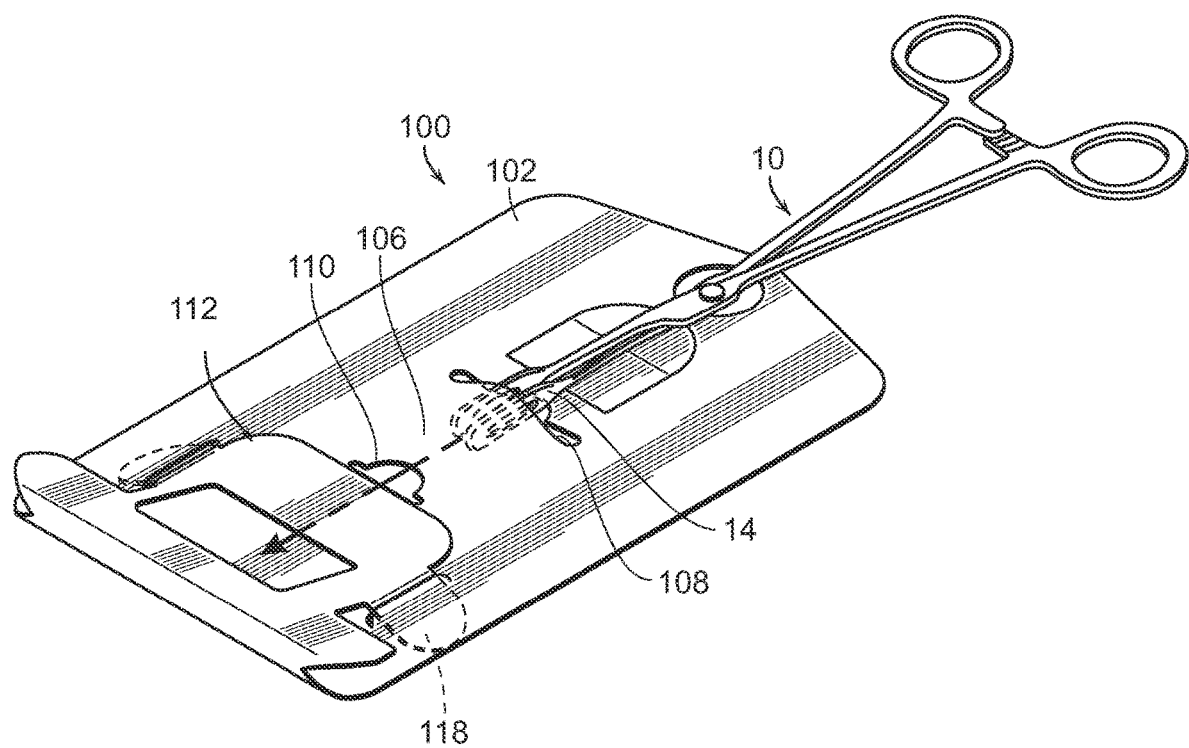
FIGS. 6-8 are top perspective views illustrating an instrument being attached to the backer card, in accordance with the present invention.

As illustrated in FIG. 6, a second end 14 of an instrument 10 is inserted into the first medical instrument receiving slot 108, so as to pass on the back surface of the support member 102, and then threaded through and inserted into the second medical instrument receiving slot 110 and then into the pocket 112. The medical instrument 10 is held to the backer card 100 by the strap 106 and by the second end 14 of the instrument 10 being positioned within the open-ended pocket 112.

Figure 7:
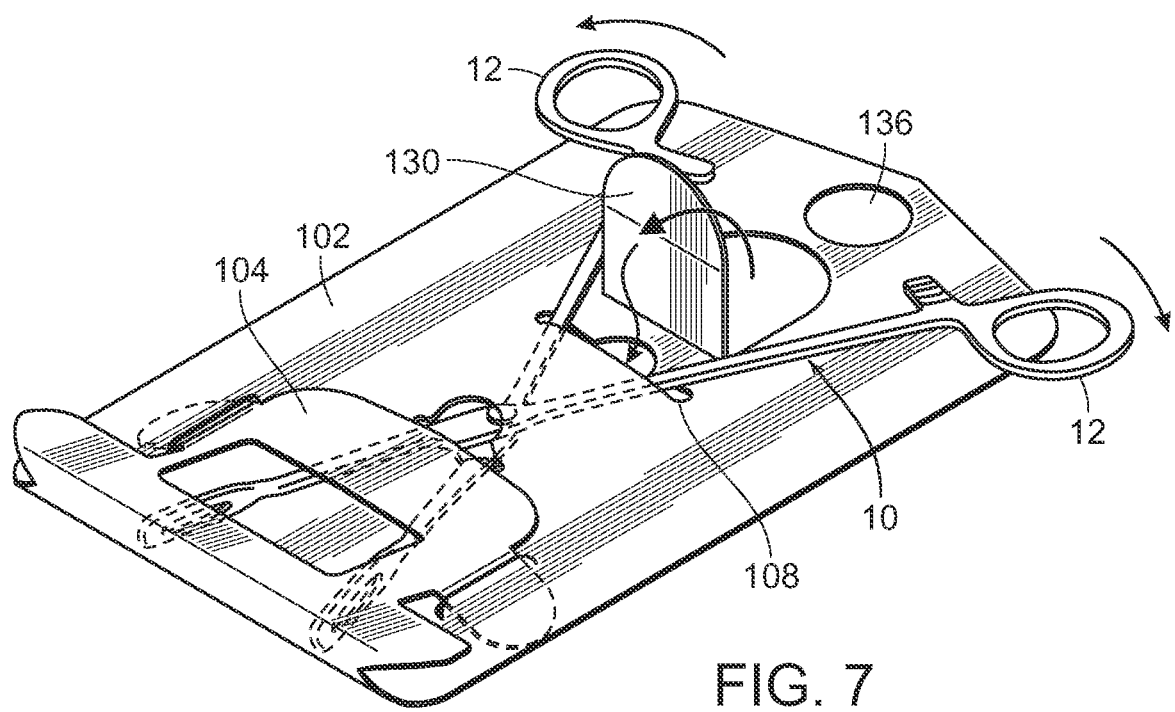

If the instrument is jointed or hinged, the handles or first end 12 of the instrument 10 are pulled away from one another, as illustrated in FIG. 7, so as to open the jointed instrument. Flap 130 is then partially detached, such as by tearing or pushing along the die cut 132, and the flap 130 is then inserted into the first instrument receiving slot 108 between arms of the instrument to retain the instrument 10 in the open position by preventing the arms thereof from moving towards one another. Use of the 14-pt. paperboard ensures that the first ends of the instrument or instrument handles 12 are not able to come towards one another and that the instrument 10 is retained in the open position, both during sterilization as well as thereafter.

It has been found that paperboard which is thinner, less than 14 pt., such as 10 pt., may sometimes fail and enable the instrument to close. Moreover, the pocket 112 formed by the relatively thick paperboard of shield member 104 and support member 102 does not require tip protectors and does not easily tear or puncture, thus the second end 14 of the instrument 10 is retained within the pocket 112.

The combination backer card 100 and attached instrument 10 can then be picked up by inserting one's finger through the fingerhold 136 in order to be placed in a sterilization package, such as a peel pouch 2 or the like.

Figure 8:
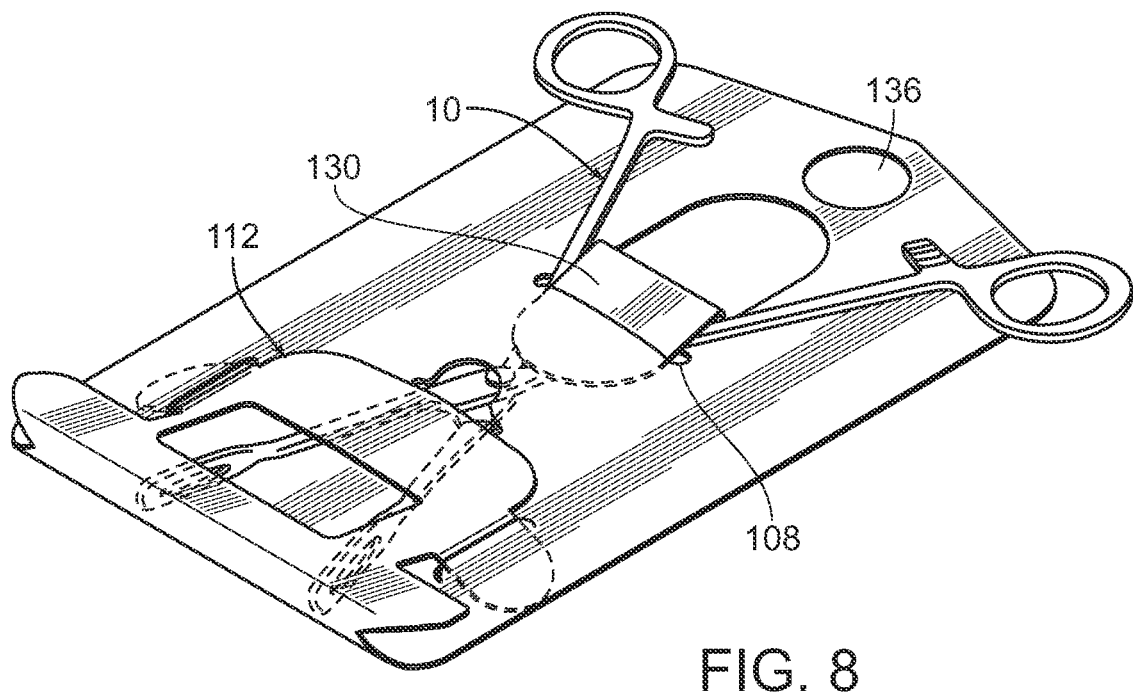
Figure 9:
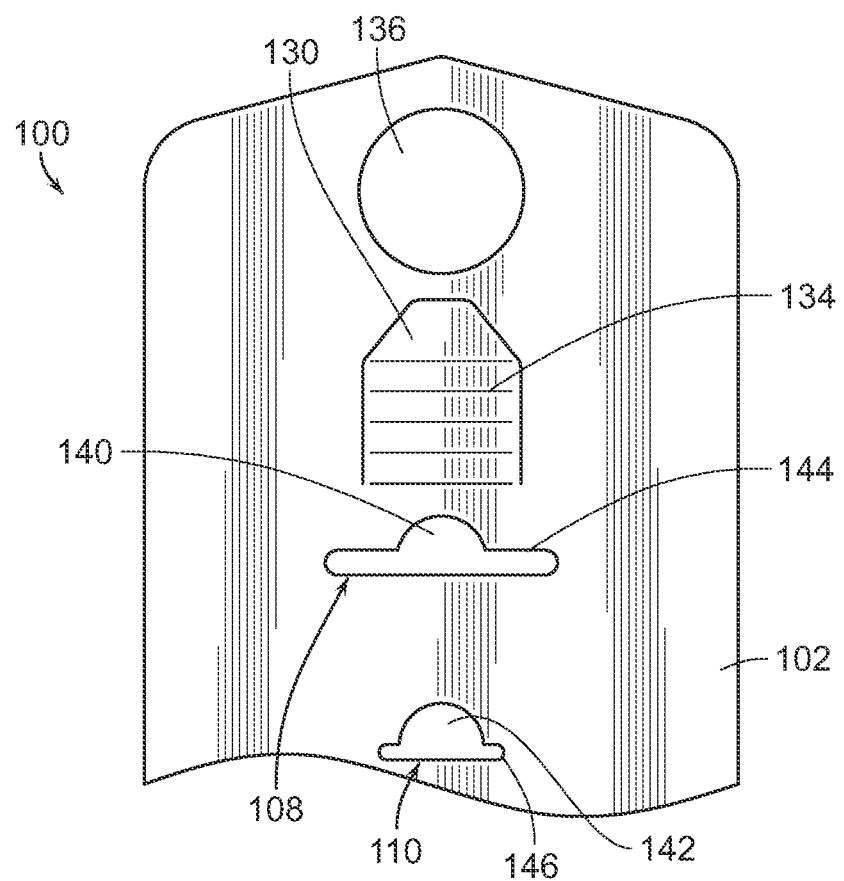
FIGS. 9-11 illustrate variations of the size and configuration of instrument receiving slots and flaps of the backer card to accommodate instruments of varying types and sizes, in accordance with the present invention.
Figure 10:
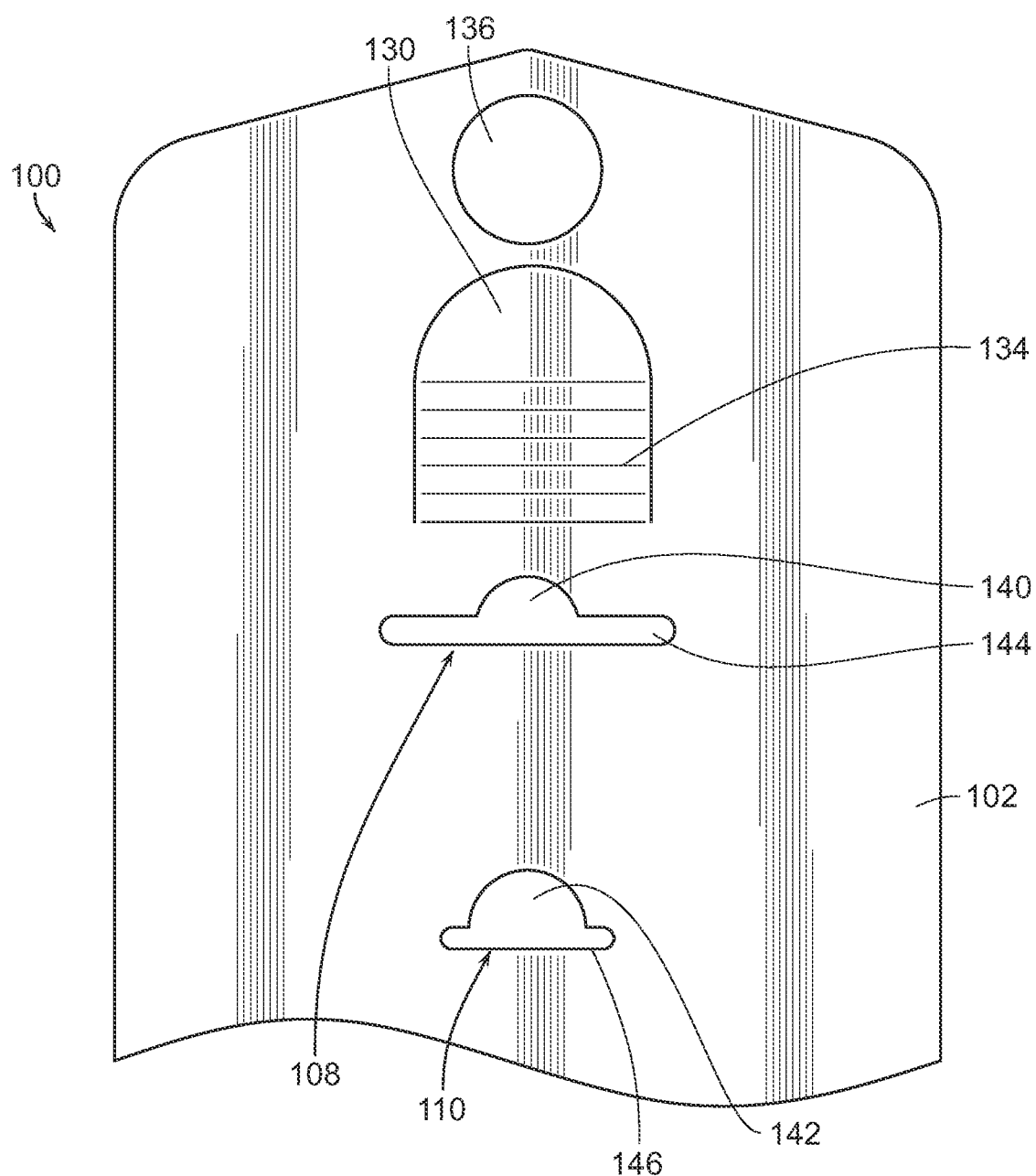
Figure 11:
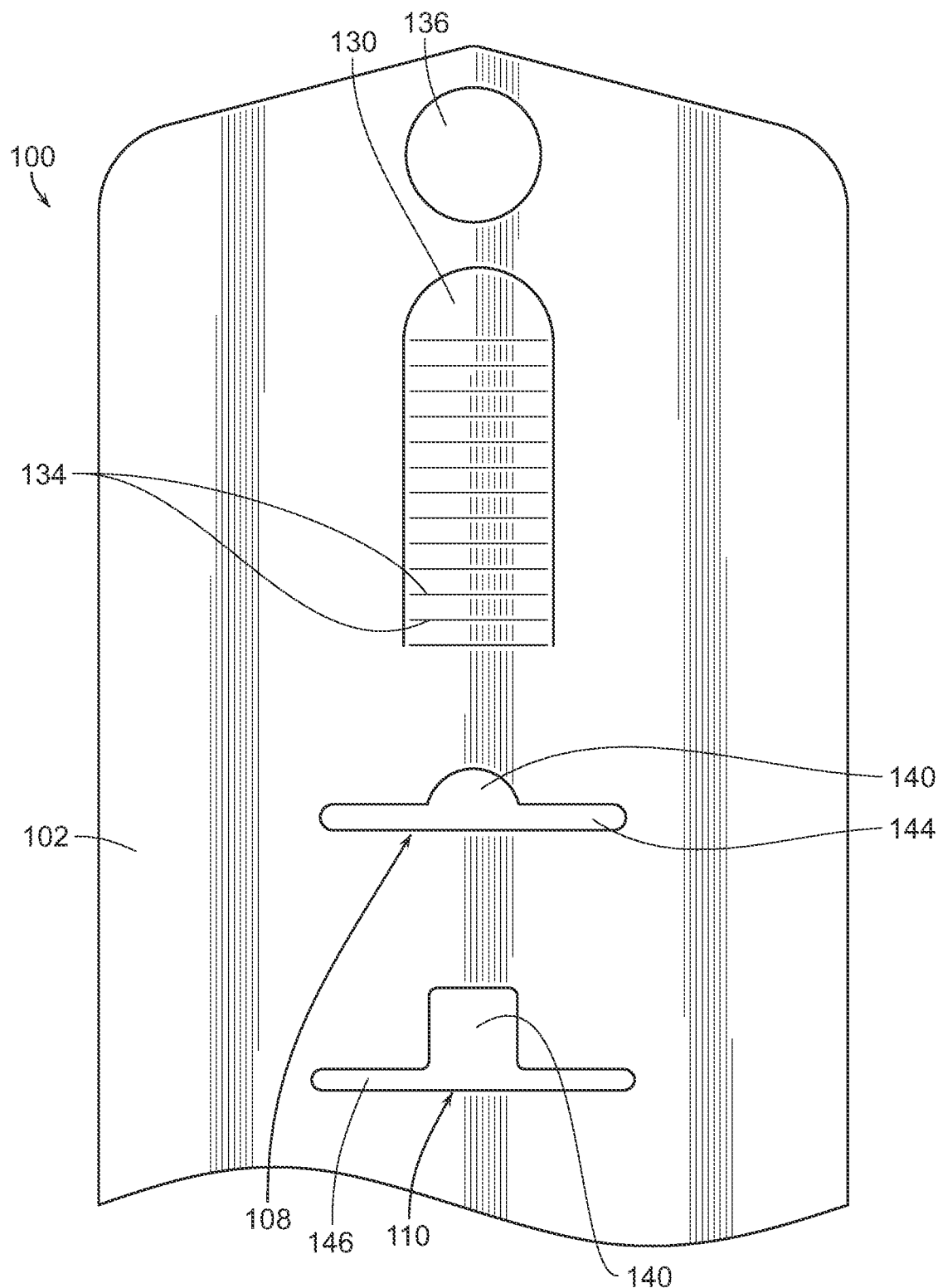

With reference now to FIGS. 9-11, the size and configuration of the first medical instrument receiving slot 108 and/or second medical instrument receiving slot 110 may vary according to the medical instruments to be held onto the backer card 100. The slots 108 and 110 are of a sufficient size so as to accommodate the insertion, and if necessary the opening or expansion, of the medical instrument therethrough. A central portion 140 and 142 of the respective first and second medical instrument receiving slots 108 and 110 is larger than side portions 144 and 146 of the slots 108 and 110. Such central portions 140 and 142 are enlarged so as to accommodate receipt of the medical instrument through the medical instrument receiving slot 108 and 110. The side portions 144 and 146 of the slots 108 and 110 are of a sufficient size in both length and width so as to receive the arms of the instrument therein when in the open position, as illustrated in FIGS. 7 and 8. It can be seen from FIGS. 9-11 that the central portions 140 and 142 of the slots 108 and 110 may have varying configurations, such as semi-circular or multi-faceted so as to accommodate insertion of the instrument therethrough, such as a hinged or jointed portion of the instrument which may be thicker or enlarged than individual arms of the instrument, which can be extended into the smaller side slot portions 144 and 146.

Similarly, the flap 130 may be of varying configurations and sizes depending upon the instrument 10 to be held by the backer card 100. Multiple score folding lines 134 may be formed on the flap 130, as needed or desired, in order to facilitate the bending and folding of the flap 130 into the first medical instrument receiving slot 108, so as to hold the instrument 10 in an open position.

Figure 12:
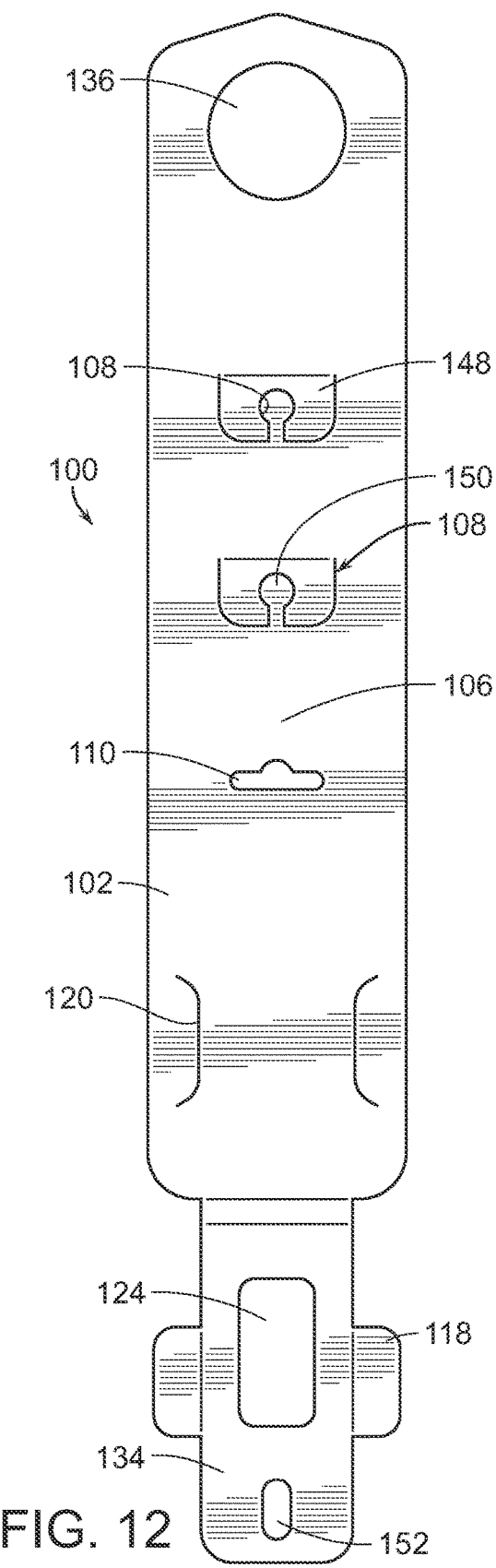
FIGS. 12 and 13 are top views of a backer card embodying the present invention usable in connection with non-jointed instruments.
Figure 13:
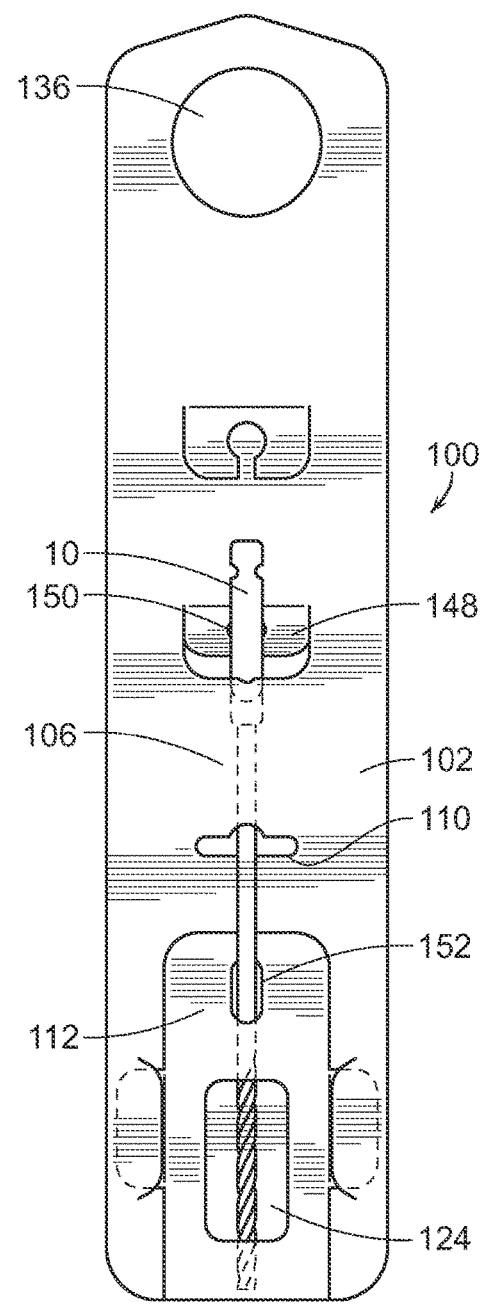

With reference now to FIGS. 12 and 13, instrument protecting backer cards 100 embodying the present invention are shown for use with non-hinged instruments, such as drill bits or the like. The backer card 100 includes a support member 102 and shield 134 movable from the non-deployed and generally planar position, as illustrated in FIG. 12, to the deployed position to form the pocket 112 as illustrated in FIG. 13, similar to that described above. Preferably, the pocket also includes a sterilant window 124. Tabs 118 of the shield 134 are insertable into shield tab slots 120 formed in the support member 102 so as to retain the shield 134 into the deployed position and attached to the support member 102.

The support member 102 also has first and second medical instrument receiving slots 108 and 110 formed therein and defining a strap 106 therebetween. The first and second medical instrument receiving slots may not need to be as wide or the central portion thereof as enlarged as is the case illustrated and described above with respect to hinged instruments, although such can vary depending upon the size and configuration of the instrument to be held by the backer card 100. In the case of simple instruments, such as the illustrated drill bit, a flap 148, which may be formed in the support member 102 by die cutting or the like, may be configured so as to directly hold the drill bit or simple instrument 10 therein, such as by having a notch 150 formed therein which partially receives the drill bit or other instrument 10 therein. The instrument is still threaded through one of the first medical instrument receiving slots 108 on the back side of the support member 102 defining the strap 106 and back through the second medical instrument receiving slot 110 and then into the pocket 112. A further retaining aperture 152 may be formed in the shield 134 through which the drill bit or other instrument 10 is inserted before being inserted into the pocket 112.

Preferably, the pocket includes a sterilant window 124, as described above, so as to provide an unobstructed access of the sterilant into the pocket 112 and also so as to visually identify the instrument 10. As illustrated in FIGS. 12 and 13, multiple first medical instrument receiving slots 108, and their accompanying flaps 148 may be formed in spaced relation on the backer card 100 so that the backer card 100 can accommodate instruments, such as the illustrated drill bit, of varying lengths. Once again, a fingerhold aperture 136 is preferably incorporated into the support member 102 for easily grasping and moving the backer card 100 and instrument 10.

Although several embodiments have been described in detail for purposes of illustration, various modifications may be made without departing from the scope and spirit of the invention. Accordingly, the invention is not to be limited, except as by the appended claims.

What is claimed is:

1. A sterilizable backer card for protecting a medical instrument, comprising:
   a support member having a strap formed integrally therewith for holding the removable medical instrument to the support member and shield tab slots formed in the support member; and
   a shield member connected to an end of the support member along a fold and movable between a non-deployed position extending away from the support member and a deployed position folded over the support member, the shield member including tabs insertable into the shield tab slots of the support member to hold the shield member over the support member in spaced apart relation thereto and form a pocket, the support member and a free end of the shield member spaced apart from the support member cooperate to define an opening of the pocket, the pocket opening being sized and configured to receive medical instruments of varying configurations, states of extension and/or sizes within the pocket, the shield member including a sterilant window that enables unobstructed contact of sterilant to the medical instrument within the pocket during sterilization of the medical instrument.

2. The backer card of claim 1, including a first medical instrument receiving slot and a spaced apart second medical instrument receiving slot formed in the support member intermediate a first end and a second end of the support member, the first and second medical instrument receiving slots cooperatively defining the strap.

3. The backer card of claim 1, wherein the sterilant window comprises a cut out formed in the shield member.

4. The backer card of claim 1, including a finger hold aperture formed in the support member.

5. The backer card of claim 2, including a flap formed by partial severance of the support member, the flap being insertable within the first medical instrument receiving slot to hold a jointed medical instrument in an open position on the support member.

6. The backer card of claim 5, wherein the flap is defined by a die cut formed in the support member.

7. The backer card of claim 5, wherein the flap has at least one score line formed thereon that facilitates bending of the flap and insertion of the flap into the first medical instrument receiving slot.

8. The backer card of claim 5, including a finger hold aperture formed in the support member in spaced relation to the flap.

9. The backer card of claim 2, wherein a central portion of the first and second medical instrument receiving slots is larger than side portions of the slot to accommodate receipt of the medical instrument through the medical instrument receiving slot.

10. The backer card of claim 1, wherein the sterilizable backer card is comprised of a paper material at least 0.014 inches in thickness.

11. The backer card of claim 1, wherein the opening to the pocket extends substantially a length of the free end of the shield member.

12. The backer card of claim 1, wherein the shield member is connected to the support member along a set of folds spaced apart a distance from one another.

13. A sterilizable backer card for protecting a medical instrument, comprising:
   a support member having a first medical instrument receiving slot and a spaced apart second medical instrument receiving slot formed in the support member intermediate a first end and a second end of the support member, the first and second medical instrument receiving slots cooperatively defining a strap for holding the removable medical instrument to the support member;
   a shield member connected to the support member along a set of folds spaced apart a distance from one another, the shield member being foldable with respect to the support member between a non-deployed position extending away from the support member and a deployed position folded over to the support member, the support member and the shield member being spaced apart from one another a distance at least partially corresponding to the distance between the set of folds to form a pocket, a free end of the shield member spaced apart from the support member and the support member cooperate to define an opening to the pocket that extends substantially a length of the free end of the shield member to receive an end of medical instruments of varying configurations, states of extension and/or sizes into the pocket; and a finger hold aperture formed in the support member.

14. The backer card of claim 13, wherein the shield member includes tabs insertable into shield tab slots formed in the support member for holding the shield member in spaced relation to the support member in the deployed position.

15. The backer card of claim 13, wherein the pocket includes a sterilant window that enables unobstructed contact of sterilant to the end of the medical instrument within the pocket during sterilization of the medical instrument.

16. The backer card of claim 15, wherein the sterilant window comprises a cut out formed in the shield member.

17. The backer card of claim 13, including a flap formed by partial severance of the support member, the flap being insertable within the first medical instrument receiving slot to hold a jointed medical instrument in an open position on the support member.

18. The backer card of claim 17, wherein the flap is defined by a die cut formed in the support member.

19. The backer card of claim 17, wherein the flap has at least one score line formed thereon that facilitates bending of the flap and insertion of the flap into the first medical instrument receiving slot.

20. The backer card of claim 13, wherein a central portion of the first and second medical instrument receiving slots is larger than side portions of the slot to accommodate receipt of the medical instrument through the medical instrument receiving slot.

21. The backer card of claim 13, wherein the sterilizable backer card is comprised of paper material at least 0.014 inches in thickness.

22. A sterilizable backer card for protecting a medical instrument, comprising:

a support member having shield tab slots formed therein;

a first medical instrument receiving slot and a spaced apart second medical instrument receiving slot formed in the support member intermediate a first end and a second end of the support member, the first and second medical instrument receiving slots cooperatively defining a strap for holding the removable medical instrument to the support member;

a flap formed by partial severance of the support member, the flap being insertable within the first medical instrument receiving slot to hold a jointed medical instrument in an open position on the support member;

a shield member connected to the support member along a set of folds spaced apart a distance from one another, the shield member being foldable with respect to the support member between a non-deployed position extending away from the support member and a deployed position folded over the support member, tabs of the shield member insertable into the shield tab slots of the support member to hold the shield member in spaced apart relation to the support member and form a pocket having a dimension corresponding to the space formed between the shield member and the support member by the tabs and the distance between the set of folds, the support member and a free end of the shield member spaced apart from the support member cooperate to define an opening to the pocket extending substantially a length of the free end of the shield member so as to receive an end of medical instruments of varying configurations, states of extension and/or sizes therethrough and into the pocket, the pocket including a sterilant window formed in the shield member that enables unobstructed contact of sterilant to the end of the medical instrument within the pocket during sterilization of the medical instrument; and a finger hold aperture formed in the support member in spaced relation to the flap.

23. The backer card of claim 22, wherein the flap is defined by a die cut formed in the support member.

24. The backer card of claim 22, wherein the flap has at least one score line formed thereon that facilitates bending of the flap and insertion of the flap into the first medical instrument receiving slot.

25. The backer card of claim 22, wherein a central portion of the first and second medical instrument receiving slots is larger than side portions of the slot to accommodate receipt of the medical instrument through the medical instrument receiving slot.

26. The backer card of claim 22, wherein the sterilizable backer card is comprised of a paper material at least 0.014 inches in thickness.

* * * * *